(12) United States Patent
Kohani

(10) Patent No.: US 6,893,098 B2
(45) Date of Patent: May 17, 2005

(54) CHAIR MOUNTED BACK SUPPORT SYSTEM

(76) Inventor: Kambiz Kohani, 7920 Grado El Tupelo, Carlsbad, CA (US) 92009

(*) Notice: Subject to any disclaimer, the term of this patent is extended or adjusted under 35 U.S.C. 154(b) by 0 days.

(21) Appl. No.: 10/681,453

(22) Filed: Oct. 7, 2003

(65) Prior Publication Data

US 2005/0073186 A1  Apr. 7, 2005

(51) Int. Cl.[7] ............................................. A47C 31/00
(52) U.S. Cl. ..................................................... 297/468
(58) Field of Search .............................. 297/485, 464, 297/468, 465, 483, 484, 486, 411.23, 411.2, 297/DIG. 6, 253

(56) References Cited

U.S. PATENT DOCUMENTS

| | | | |
|---|---|---|---|
| 1,332,328 A * | 3/1920 | Fisher ......................... 297/484 |
| 2,758,769 A * | 8/1956 | Nunn et al. ................. 119/770 |
| 2,833,344 A * | 5/1958 | Lucht .......................... 297/465 |
| 2,877,833 A * | 3/1959 | Boles ......................... 297/485 |
| 3,108,589 A * | 10/1963 | Staggs ........................... 602/4 |
| 3,174,798 A | 3/1965 | Spraque |
| 4,050,737 A | 9/1977 | Jordan |
| 4,108,170 A | 8/1978 | Spann |
| RE29,811 E | 10/1978 | Norris |
| 4,117,840 A | 10/1978 | Rasure |
| 4,303,041 A | 12/1981 | Thompson et al. |
| 4,751,923 A * | 6/1988 | Marino ........................... 602/4 |
| 4,795,176 A | 1/1989 | Harrigan et al. |
| 5,086,762 A | 2/1992 | Chee |
| 5,176,622 A | 1/1993 | Anderson et al. |
| 5,396,906 A | 3/1995 | Harrold |
| 5,445,601 A | 8/1995 | Harlow |
| 5,447,498 A | 9/1995 | Watson |
| 5,503,620 A | 4/1996 | Danzger |
| 5,529,383 A | 6/1996 | Laco |
| 5,540,239 A | 7/1996 | McClellan |
| 5,953,774 A | 9/1999 | Arndt |
| 6,068,606 A | 5/2000 | Castel et al. |
| 6,095,613 A * | 8/2000 | Ostrander et al. .......... 297/467 |
| 6,361,478 B1 | 3/2002 | Giancaspro |
| 6,435,614 B1 * | 8/2002 | Gollahon ................. 297/344.1 |
| 6,436,065 B1 | 8/2002 | Mitchell |
| 6,575,530 B1 | 6/2003 | Fischer et al. |
| 6,742,848 B2 * | 6/2004 | Ruff ........................... 297/485 |
| 2002/0000747 A1 | 1/2002 | Hee |

* cited by examiner

*Primary Examiner*—Milton Nelson, Jr.
(74) *Attorney, Agent, or Firm*—Nydegger & Associates

(57) ABSTRACT

A chair mounted lumbar and trapezius support system that offers the support for an individual required to work leaning forward in an office style chair for a prolonged period of time. The device reduces the strain on the back by supporting the individual in the abdominal area of body. Adjustable elbow rests mount to the support belt structure to support the elbows and allow maximum movement of the arms while remaining in a fixed position with relation to the torso when a individual is leaning forward or twists to one side or the other doing delicate work. The support belt structure is either permanently or removably attachable to an office chair using fasteners, belts or a flexible support.

14 Claims, 5 Drawing Sheets

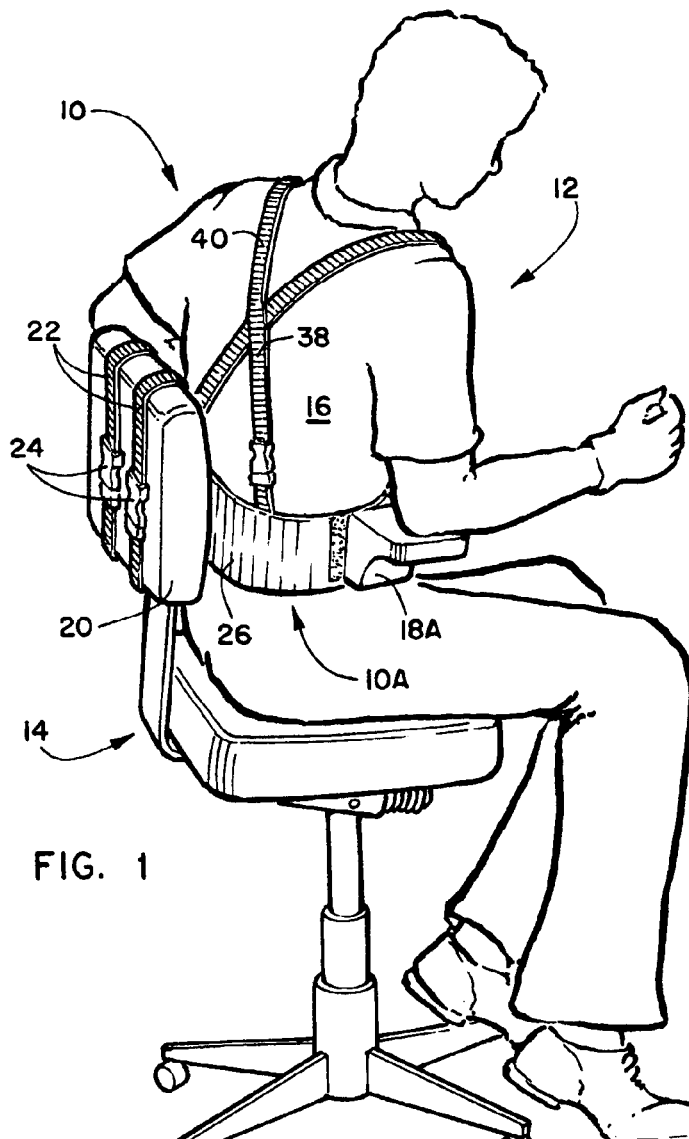
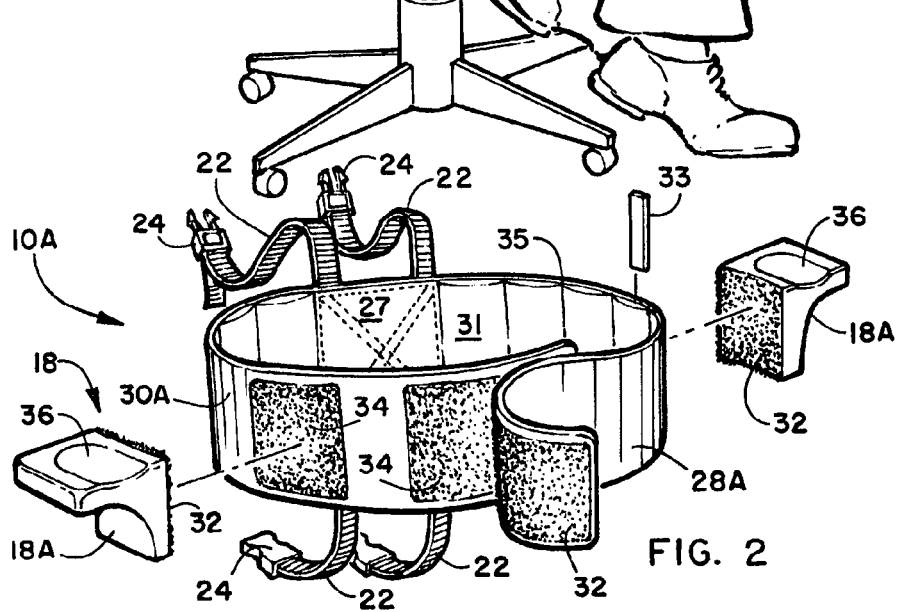
FIG. 1
FIG. 2

US 6,893,098 B2

CHAIR MOUNTED BACK SUPPORT SYSTEM

FIELD OF THE INVENTION

This invention relates to the field of supporting devices used by an individual in a sitting position who is required to lean forward. Furthermore, this individual is often required to twist and raise his or her arms to perform repetitive arduous tasks in this position for prolonged periods of time.

This invention provides a chair support system that allows the individual to lean forward and be supported by his abdominal and rib cage areas, while relieving the strain on the lumbar area of the back. Adjustable elbow rests are also incorporated into the invention to relieve the tension on the trapezius muscles along with other muscles of the upper back incurred when lifting the arms and leaning forward.

Furthermore, this invention has the distinct capability of being used by disabled individuals for support of the upper torso in the upright position with the option of leaning forward using adjustable elbow rests, i.e. to be used while working on a computer.

BACKGROUND OF THE INVENTION

This new and unique chair mounted lumbar and trapezium support system has been designed by a dentist who has suffered with back problems for years due to the many hours in the position of leaning and twisting over patients while doing precise and delicate work on their teeth. Holding up the arms for prolonged periods of time in this position creates further stress and tension on the upper back, shoulders and neck resulting in stinging pains in those areas. Conventional armrests on chairs often bump the patients in the head when the chair is moved too close and when you twist your body and lean, the armrest is no longer functional.

A technical definition of the muscles of the spine consists of the muscles of the spine covered by more-superficial back muscles, such as the trapezius and latissimus dorsi. The spinal extensors, or erector spinae, include superficial and deep layers. The relatively superficial layer can be divided into spinaIuis, longissimus, and iliocostalis divisions. In the lower lumbar and sacral regions, the boundary between the longissimus and iliocostalis muscles becomes indistinct, and they are sometimes known as the sacrospinalis muscles. When contracting together, the erector spinae extend the spinal column. When the muscles on only one side contract, the spine is bent laterally.

The spinalis muscles of the spine interconnect and stabilize the vertebrae. These muscles include the semispinalis muscles and the multifidus, interspinales, intertransversarii, and rotators. In various combinations, they produce slight extension or rotation of the spinal column. They are also important in making delicate adjustments in the positions of individual vertebrae, and they stabilize adjacent vertebrae. If injured or strained, these muscles can start a cycle of pain, muscle stimulation and contractions in the lower back. This cycle can lead to pressure on adjacent spinal nerves leading to sensory losses as well as limiting mobility.

The large, superficial trapezius muscles cover the back and portions of the neck, reaching to the base of the skull. These muscles originate along the midline of the neck and back and insert on the clavicles and the scapular spines. The trapezius muscles are enervated by more than one nerve and specific regions can be made co contract independently. As a result, their actions are quite varied. The trapezius action depends on the active region and state of other muscles. They may elevate, retract, depress, or rotate scapula upward, elevate clavicle and also extend head and neck. In like manner, if injured or strained, these muscles can start a cycle of pain, muscle stimulation and contractions in the neck and shoulders.

Many of the warm-up and stretching exercises recommended before athletic events are intended to prepare these very important muscles for their supporting role, but in many cases individuals are not in the position nor have the time to perform these vital exercises prior to working in these positions for a long period of time.

Originally invented for dentists, this inventor has found that this new and unique device has many additional uses in related fields where physicians and surgeons are required to work over patients for prolonged periods of time. Additional fields where the device will find a great deal of use will include the support of the handicapped in a sitting position.

References Cited

U.S. Pat. No. 5,396,906 of David W. Harrold describes a back support belt having inflatable bladder members mounted on the inner surface of the belt to engage and support the lower back. A pump is further provided for inflating and deflating the bladder. The pump is integrally attached to the belt and includes a valve operable to permit inflation and deflation of the bladder and a conduit for fluid communication between die pump, valve and the bladder.

This back support belt is to be used by an active person, not an individual in a sitting position, and having no attachment to the chair, it would not relieve the stress incurred when leaning forward in a sitting position.

U.S. Pat. No. 5,445,601 of Robert R. Harlow teaches of a lower back support device for use in applying force to the lumbar vertebrae of the human spinal column. The device has a support plate attached to a pair of inner bands for encircling the wearers' body to position the support plate. It also has a one-piece outer band which fastens to its outside of the inner band to pass the plate toward the back of the wearer.

This is another back support belt that is to be used by an active person, not an individual in a sitting position, and having no attachment to the chair, it would not relieve the stress incurred when leaning forward in a sitting position.

U.S. Pat. No. 5,447,498 of George W. Watson discloses an elongated semi-flexible woven lumbar support belt that has a wide central support portion and a pair of inter-connectable opposite end portions which are significantly narrower than the central support portion. The central support portion is formed from webbing having a plurality of warp strands interwoven with a plurality of weft strands. The warp and weft strands, respectively, are fixedly attached to each other at angular junctions such that the stiffness of the webbing is greater than if the strands were not fixedly attached with each other at the angular junctions. The warp strands are spaced apart from each other and the weft strands likewise are spaced apart from each other to provide ventilation through the webbing.

This is still another back support belt to be used by an active person, not an individual in a sitting position, and having no attachment to the chair, it would not relieve the stress incurred when leaning forward in a sitting position.

U.S. Pat. No. 5,503,620 of Joshua Danzger additionally describes a back support belt comprising a primary support belt including fasteners for fastening the same, generally at the frontal area of the waist of the wearer. A secondary tensioning belt comprising fasteners for fastening the same around the primary support belt generally at the frontal area of the waist of the wearer is provided. It includes back support belt color tensioning indicators on the secondary tensioning belt which are visible only from the rear and side areas of the waist of the wearer, and thus not by the wearer, and which are operable to indicate both when the back support belt is property tensioned around the waist of the wearer and when the back support belt is not property tensioned around the waist of the wearer. The back support belt color tensioning indicators are operable to indicate proper and improper tensioning of the support belt independently of the relationship between the size of the support belt and the waist size of the wearer to thus be virtually foolproof.

This is still another back support belt that is to be used by an active person and not an individual in a sitting position, and having no attachment to the chair, it would not relieve the stress incurred when leaning forward in a sitting position.

U.S. Pat. No. 5,529,383 of Randall J. Laco tells of a device for retaining the user in a substantially upright position when seated in a chair. The device consists of a bracket attached to the back of the chair having two distal ends extending laterally outward from the back support portion of the chair. Attached to these distal ends is an adjustable, padded strap that supports the abdomen of the person seated in the chair to prevent them from slouching or leaning forward. The strap extends perpendicular to the rear strut or frame of the chair to hold the user firmly in an upright position.

This invention is intended to support an individual in an upright position by means of a padded strap that supports the abdomen. This device does not allow the individual to lean forward and does not supply any form of adjustable elbow supports.

U.S. Pat. No. 6,068,606 of John C. Castell et al. describes a back brace for supporting the back of a wearer of the brace for preventing injuries and reinforcing proper lifting mechanics during lifting activities.

This is still another back support belt that is to be used by an active person, not an individual in a sitting position, and having no attachment to the chair, it would not relieve the stress incurred when leaning forward in a sitting position.

U.S. Pat. No. 6,575,530 of Harry Fisher et al. discloses a device for lumbar support for an office chair having a seatback including a seatback frame and a membrane stretched over the seatback frame. The device can be arranged behind the membrane and can be housed in the seatback frame to provide vertical and horizontal adjustment independent of the membrane. Preferably, the device includes a central part having two comparably rigid carrier elements connected to each other via an elastic element arranged there between the rigid carrier elements each including a guide track that can be arranged in the seatback frame to provide the vertical adjustment. A front pad includes a cushion attached to an upholstery plate, the upholstery plate facing the membrane. A rear part includes a plastic plate. The cushion and the plastic plate are connected via a clip connection, and the clip connection is guided in slots of the carrier elements.

Although this device deals with the backrest of a conventional office chair and aids in the support of the lumbar area of the back, its purpose is achieved when the individual using the chair leans back against the backrest. It gives no support when leaning forward and does not offer the unique adjustable elbow rests.

Consequently there exists a need for an apparatus which will support and relieve the stress of an individual leaning forward in a chair for a prolonged period of time. None of the foregoing prior art teaches or suggests the particular unique features of the chair mounted lumbar and trapezius support system.

SUMMARY OF THE INVENTION

In this respect, before explaining at least one embodiment of the invention in detail, it is to be understood that the invention is not limited in its application to the details of construction and to the arrangement, of the components set forth in the following description or illustrated in the drawings. The scope of the invention is capable of other embodiments and of being practiced and carried out in various ways. Also, it is to be understood that the phraseology and terminology employed herein are for the purpose of description and should not be regarded as limiting.

The preferred embodiment of this invention consists of a chair mounted lumbar and trapezius support system that is attached to the chair rest by the means of one or more mounting straps. The preferred embodiment or simplest version of the chair mounted lumbar and trapezius support system will have adjustable elbow rests attached to the support belt. The support belt structure is composed of a central reinforced back element held rigidly to the chair backrest. The left side element and right side element consist of semi-flexible material with substantial padding and conventional hook fastening surface and loop fastening surface in the front. The shape of the support belt structure can be straight on both edges or can be relieved in the area of the individual's thighs. Common plastic supporting stays may run in a horizontal direction or in a vertical direction within the supportive structure to maintain the basic shape of the device. The configuration of the adjustable elbow rests will vary from the angular design shown in the drawings to other convenient shapes including square. The adjustable elbow rests move up and down, along with making angular adjustments so the individual has a stable resting platform for their elbows while doing delicate work while still giving a broad range of arm movement. The elbow rests relieve the stress on the trapezius muscles of the back and shoulders incurred when holding the arms up and doing precise and delicate work for a prolonged period of time.

A second alternate embodiment of the chair mounted lumbar and trapezius support system will have shoulder straps to relieve the pressure exerted on the adjustable elbow rests.

A third alternate embodiment of the chair mounted lumbar and trapezius support system will have an added torso support unit. The device will consist of a support belt structure having the central reinforced back element held to the chair backrest with a left side element and a right side element. The left side element and right side element consist of a semi-flexible material with substantial padding and a conventional hook fastening surface on the inside of each distal protruding end. The addition of the torso support unit allows for a greater adjustment of waist sizes of the individuals using the device. The torso support unit consists of a belt clasping at the back by the means of a side squeeze buckle. The frontal section of the torso support unit is comprised of a torso support with an elastic insert in the central lower section to relieve excessive pressure in the area of the groin while retaining the support in the area of the upper abdomen and rib cage. The torso support unit will have a loop fastening means on either side to match the hook-fastening surface on the insides of the left side element and the right side element. The adjustable elbow rests will attach to the sides of the left side element and the right side element as they do in the other embodiments of the chair mounted lumbar and trapezius support system.

An alternate embodiment of the adjustable elbow rest will pivot outwardly from the back. This alternate embodiment of the adjustable elbow rest has a mounting plate with a loop fastening surface on the back and the rest member pivoting outwardly from the back edge of the mounting plate by the means of the hinge mechanism. The left side of the adjustable elbow rest will be a mirror image of the right side. The hinge mechanism could be at the front of the adjustable elbow rest allowing the adjustable elbow rest to pivot from the front, or there could be a double hinge mechanism pivoting from both the front and back.

All the embodiments of the chair mounted lumbar and trapezius support system may be configured with a flexible support member between the chair backrest mounting straps and the support belt structure to give a cushioned resistance while giving a greater forward leaning mobility. Noticeably in this configuration the adjustable armrests stay in a fixed relationship to the torso of the individual.

As such, those skilled in the art will appreciate that the conception, upon which this disclosure is based, may readily be utilized as a basis for designing of other structures, methods, and systems for carrying out the several purposes of the present invention. It is important, therefore, that the claims be regarded as including such equivalent construction insofar as they do not depart from the spirit and scope of the present invention.

THE OBJECTS OF THIS INVENTION ARE

The object of this invention is to create a means to support the back of an individual with relation to the backrest of the chair.

Another object of this invention is to create a means to support the back of an individual required to lean directly forward, or lean forward and twist his body while sitting in a chair.

Another object of this invention is to create a means to support an individual leaning forward in a chair with a uniform pressure over his abdominal muscles and rib cage.

Another object of this invention is to create adjustable elbow rests rather than armrests to allow full movement of the arms while relieving the neck and shoulder strain of holding the arms up and doing delicate work in this position for prolonged periods of time.

Yet another object of this invention is to create a means to attach adjustable elbow rests that stay in position relative to the body when an individual is required to twist or move his upper torso.

A further object of this invention is to create a chair mounted lumbar and trapezius support system that will fit any waist size of the individual using it and still give adequate support.

Even still another object of this invention is to create a chair mounted lumbar and trapezius support system that can be incorporated as an integral part of the backrests of conventional office chairs.

A final object of this invention is to create a chair mounted lumbar and trapezius support system that can be used not only by doctors and dentists but equally well by the handicapped or anyone required to lean forward in a chair for prolonged periods and requiring some support at the elbows.

These together with other objects and advantages which become subsequently apparent reside in the details of the construction and operation as more fully hereinafter described and claimed, reference being had to the accompanying drawings forming a part thereof, wherein like numerals refer to like parts throughout.

There has thus been outlined rather broadly the more important features of the invention in order that the detailed description thereof that follows may be better understood, and in order that the present contribution to the art may be better appreciated. There are additional features of the invention that will be described hereinafter and which will form the subject matter and scope of the claims appended hereto.

BRIEF DESCRIPTION OF THE DRAWINGS

The accompanying drawings, which are incorporated in and form a part of this specification, illustrate embodiments of the invention and together with the description, serve to explain the principles of this invention.

FIG. 1 depicts a perspective view of an individual sitting in a conventional office style chair leaning forward and twisting his upper torso using the chair mounted lumbar and trapezius support system with adjustable elbow rests.

FIG. 2 depicts a perspective view of the preferred embodiment or simplest version of the chair mounted lumbar and trapezius support system with adjustable elbow rests exploded to the sides.

DETAILED DESCRIPTION OF THE PREFERRED EMBODIMENTS

Figure 3:
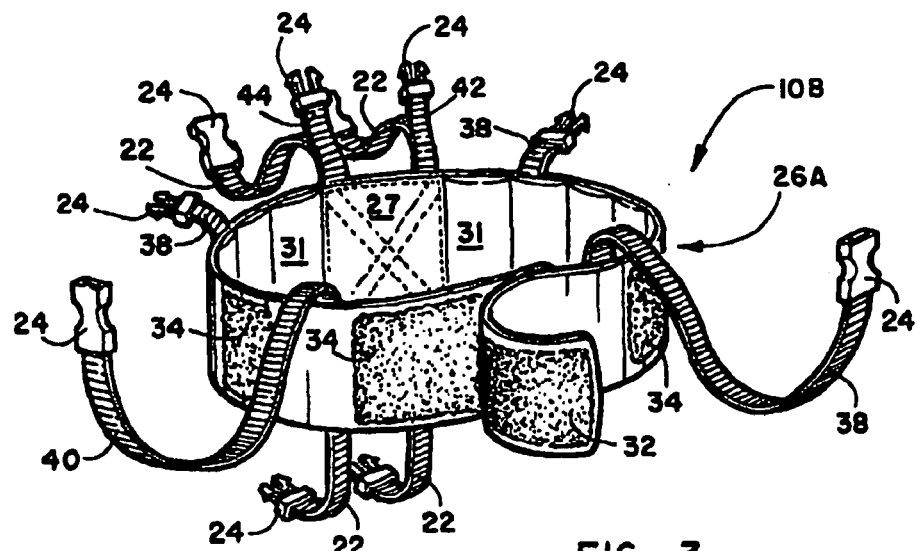
FIG. 3 depicts a perspective view of an alternate embodiment of the chair mounted lumbar and trapezius support system with the added shoulder straps.

Referring now to the drawings of FIG. 1–14, wherein similar parts of the invention are identified by like reference numerals, there is seen in FIG. 1 a perspective view of the disclosed device 10 in a first preferred embodiment of a system 10A for back support showing an individual 12 sitting in a conventional office style chair 14 leaning forward and twisting his upper torso 16 using the system 10A for chair mounted back support which as noted above is especially supportive of the lumbar and trapezius areas of the body. Also shown is the adjustable elbow rests 18A attached to the backrest 20. However, the device 10 is a substantial improvement in providing support to leaning workers without the elbow rest 18A and though it would provide great utility and improvement in such support of leaning individuals 12 such as doctors and dentists, it functions best with it by allowing a support for the elbow giving the occupant a much steadier hand during procedures requiring dexterity.

In the preferred embodiment of the device 10 shown the chair mounted lumbar and trapezius support system 10A is attached to the chair backrest 20 by the means of attachment communicating between the chair and the support belt structure 26A which as shown features one or a plurality of mounting straps 22 secured to or around the chair 14. The means of attachment to the chair whether it be mounting straps 22 or some other means of attachment, can either be permanent or allow for easy attachment and removal and adjustment of the support belt 26. In cases where the user moves from office to office and chair to chair, it is envisioned that the user would wear the support belt 26 continually and attach it to different chairs 14 in different locations using a separable fastener such as buckle 24 which separates into two halves with the buckle 24 engaging any of a plurality of buckles 24 attached to different chairs 14. This would allow the user to secure the support belt 26 on their person and then easily move from chair to chair with a simple engagement of the buckle 24 to the chair 14 at each stop. As depicted in FIG. 1, straps 22 are attached at their distal ends using a means for fastening such as the depicted side squeeze buckles 24 for a semi-permanent attachment to the chair 14 so that multiple users could use the same support belt 26 attached to an individual chair 14. Of course those skilled in the art will realize that numerous means of attachment of the different embodiments of the support system 10 herein described could be used as long as the support system is secured to the chair 14 during use which provides support against the leaning individual 12, and any such permanent, semi-permanent, or removable means of attachment of the support belt 26 to the chair 14 for the desired permanent or temporary mount is anticipated.

FIG. 2 depicts a perspective view of a first preferred embodiment and simplest version of the chair mounted support system 10A with one or a plurality of adjustable elbow rests 18A exploded to the sides. The support belt structure 26A is composed of a central reinforced back element 27 that is held adjacent to the chair backrest 20 using a means of attachment thereto. The left side element 28 and right side element 30 consist of a semi-flexible material with substantial padding 31 and a means of adjustable attachment of the distal ends of the left side element 28 to the right side element 30 shown as conventional hook fastening surface 32 which engages loop fastening surface 34 in the front. Should extra support be desired, plastic supporting stays 33 may run in a horizontal direction or in vertical direction within pockets 35 formed in the support belt structure 26A. These stays 33 might be sewn in permanently or could be optionally provided in a kit of stays 33 to be inserted by the user if desired.

As noted, the elbow rests 18 can be provided at one or both sides to provide support to the elbow and thus the arms of the user during use. The configuration of the adjustable elbow rests 18A and 18B may vary from the angular design shown in the drawings to other shapes including square and still remain within the scope of the invention. If the elbow rests 18 are not permanently mounted, they would be attached to the device 10 using a means of removable attachment to the support belt 26. As depicted in FIGS. 1 and 2, the elbow rests 18 are depicted as adjustable elbow rests 18A which are shown attached to the support belt structure 26A by the means of the hook fastening surface 32 and loop fastening surface 34 to allow means for vertical and horizontal and angular adjustment which is inherent when using hook and loop fabric fasteners for such attachments. Consequently, the device 10 provides the user with elbow support from the elbow rests 18 which when provided as removable adjustable elbow rests 18A and 18B can be easily adjusted to fit the body and working environment of every user. The fasteners attaching the elbow rests 18A and 18B to the support belt 26 would therefore provide one or a plurality of means for adjustment including a means for horizontal adjustment, a means for vertical adjustment, and a means for angular adjustment of the individual elbow rests 18A and 18B. While a removable mount with hook and loop fabric is the preferred means for attachment of the elbow rests 18A and 18B to the support belt 26 in its various embodiments, the adjustable elbow rests 18A and 18B could be mounted in fixed positions or with other attachment means such as snap style fasteners or brackets to the support belt structure 26A and still remain within the scope of this invention. An optional elbow rest depression 36 or a depression 36 that is temporarily formed in a viscoelastic temperature sensitive foam, may be added to the adjustable elbow rests 18A for an especially comfortable support of the elbow of the individual using the device.

FIG. 3 depicts a perspective view of an alternate preferred embodiment of the chair mounted support system 10B with the added shoulder straps 38 and 40 attached by the means of the side squeeze buckles 24. As depicted in FIG. 1, these shoulder straps 38 and 40 can be attached at the front of the support belt structure 26A and communicate to an attachment on the sides of the support belt structure 26A or at the back to the straps 42 and 44. Addition of the shoulder straps 38 and 40 would be an optional component that can be attached to relieve the downward pressure on the support belt structure 26A when resting the elbows on the adjustable elbow rests 18A or 18B.

Figure 4:
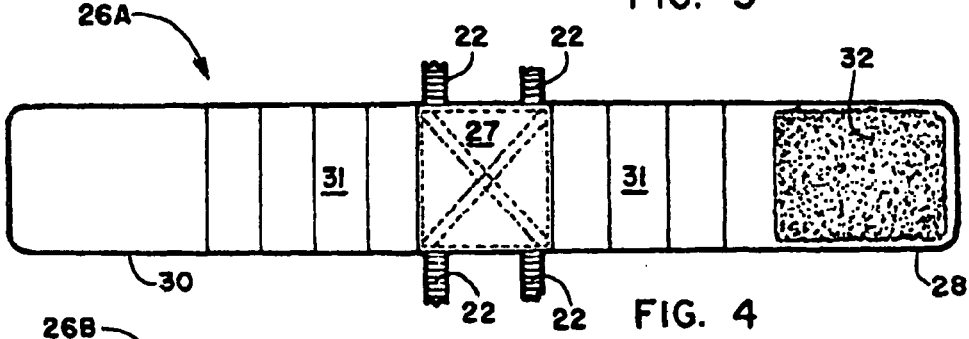
FIG. 4 depicts a flat pattern layout of the preferred embodiment of the chair mounted lumbar and trapezius support system.
Figure 5:
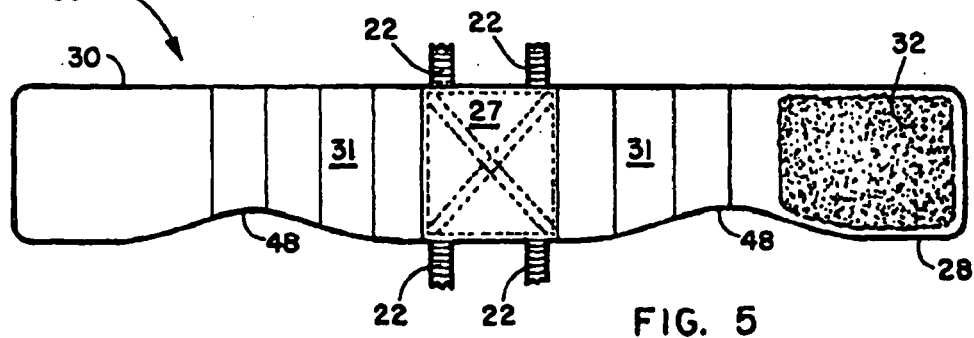
FIG. 5 depicts a flat pattern layout of a second alternate embodiment of the chair mounted lumbar and trapezius support system relieved on both sides in the area of the thighs.

This depicted embodiment of the chair mounted support system 10B also retains the support belt structure 26A that is composed of a central reinforced back element 27 to be held adjacent to the chair backrest 20 and the left side element 28 and the right side element 30 (as shown in FIGS. 4 and 5). The left side element 28 and right side element 30 also consist of a semi-flexible material with substantial padding 31 and conventional hook fastening surface 32 engaging loop fastening surface 34 in the front.

FIG. 4 depicts a flat pattern layout of the support belt structure 26A of a separate preferred embodiment of the chair mounted system 10A and 10B while FIG. 5 depicts a flat pattern layout of the support belt structure 26B of the chair mounted support system 10A and 10B with the addition of a thigh relief 48 on both sides. Both of these support belt structures 26A and 26B are composed of a central reinforced back element 27 to be held to the chair backrest 20 or other chair attached support used for attachment and the left side element 28 and the right side element 30. The left side element 28 and right side element 30 also consist of a semi-flexible material preferably with substantial padding 31 and an adjustable means to attach the distal ends of the side elements shown in the form of hook fastening surface 32 loop fastening surface 34 in the front.

Figure 6:
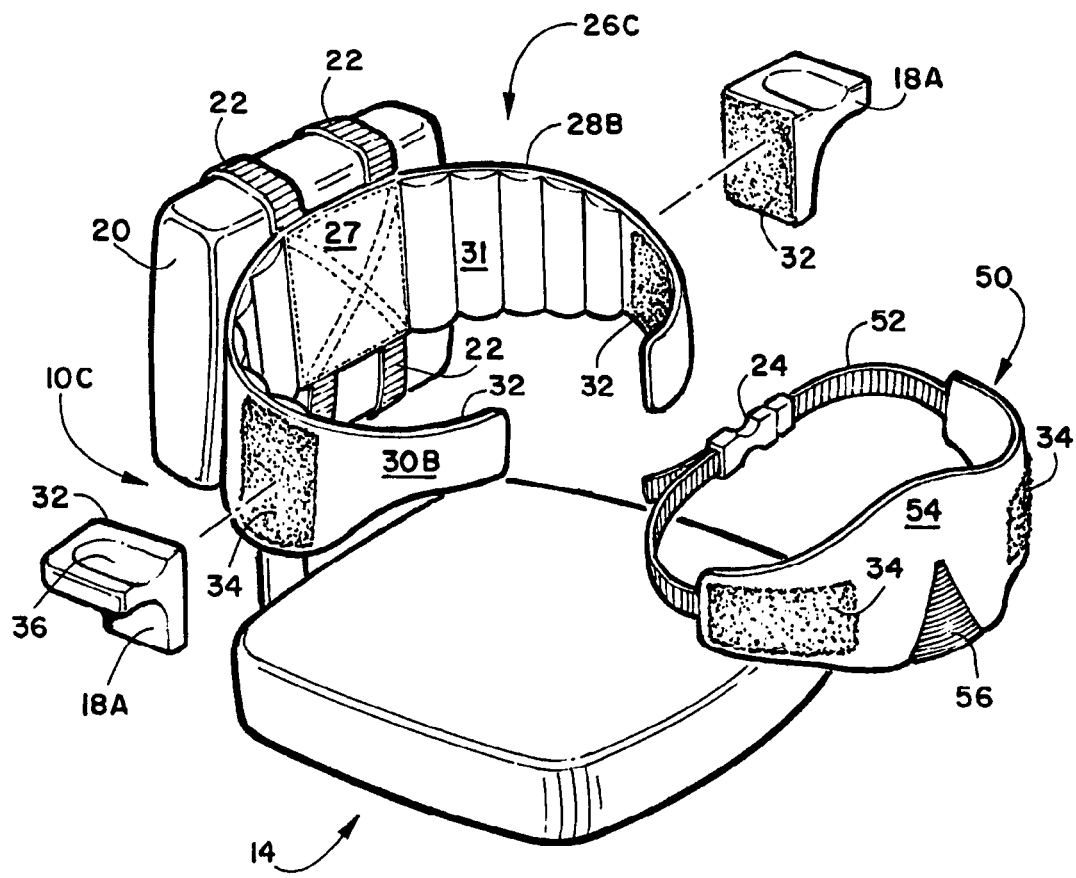
FIG. 6 depicts a perspective view of a third alternate embodiment of the chair mounted lumbar and trapezius support system with the added torso support unit and the adjustable elbow rests exploded to the sides.

FIG. 6 depicts a perspective view of a third alternate embodiment of the chair mounted support system 10C with the added torso support unit 50 and the adjustable elbow supports 18A exploded to the sides. This third alternate embodiment of the chair mounted support system 10C will consist of a support belt structure 26C having the central reinforced back element 27 held to the chair backrest 20 and the left side element 28B and the right side element 30B. The left side element 28B and right side element 30B also consist of a semi-flexible material preferably with substantial padding 31 and means to adjustably attach the distal ends of the side elements shown as conventional hook fastening surface 32 on the inside of each distal end.

The addition of the torso support unit 50 allows for a greater adjustment of waist sizes of the individuals 12 using the device. The torso support unit consists of a belt 52 and a means of attachment of the belt 52 around the torso of a user shown as side squeeze buckles 24. The frontal section of the torso support unit 50 is comprised of a torso support 54 attached at either side to the belt 52 with an elastic insert 56 in the central lower section to relieve excessive pressure in the area of the groin while retaining the support in the area of the rib cage. The torso support unit 50 will have a loop fastening surface 34 on either side to match the hook fastening surface 32 on the insides of the distal ends of left side element 28B and the right side element 30B. The adjustable elbow rests 18A and 18B will attach to the sides of the left side element 28B and the right side element 30B as they do in the other embodiments of the chair mounted lumbar and trapezius support system 10A and 10B. This embodiment would be especially useful for individuals with a larger waist or for those who need additional frontal torso support.

Figure 8:
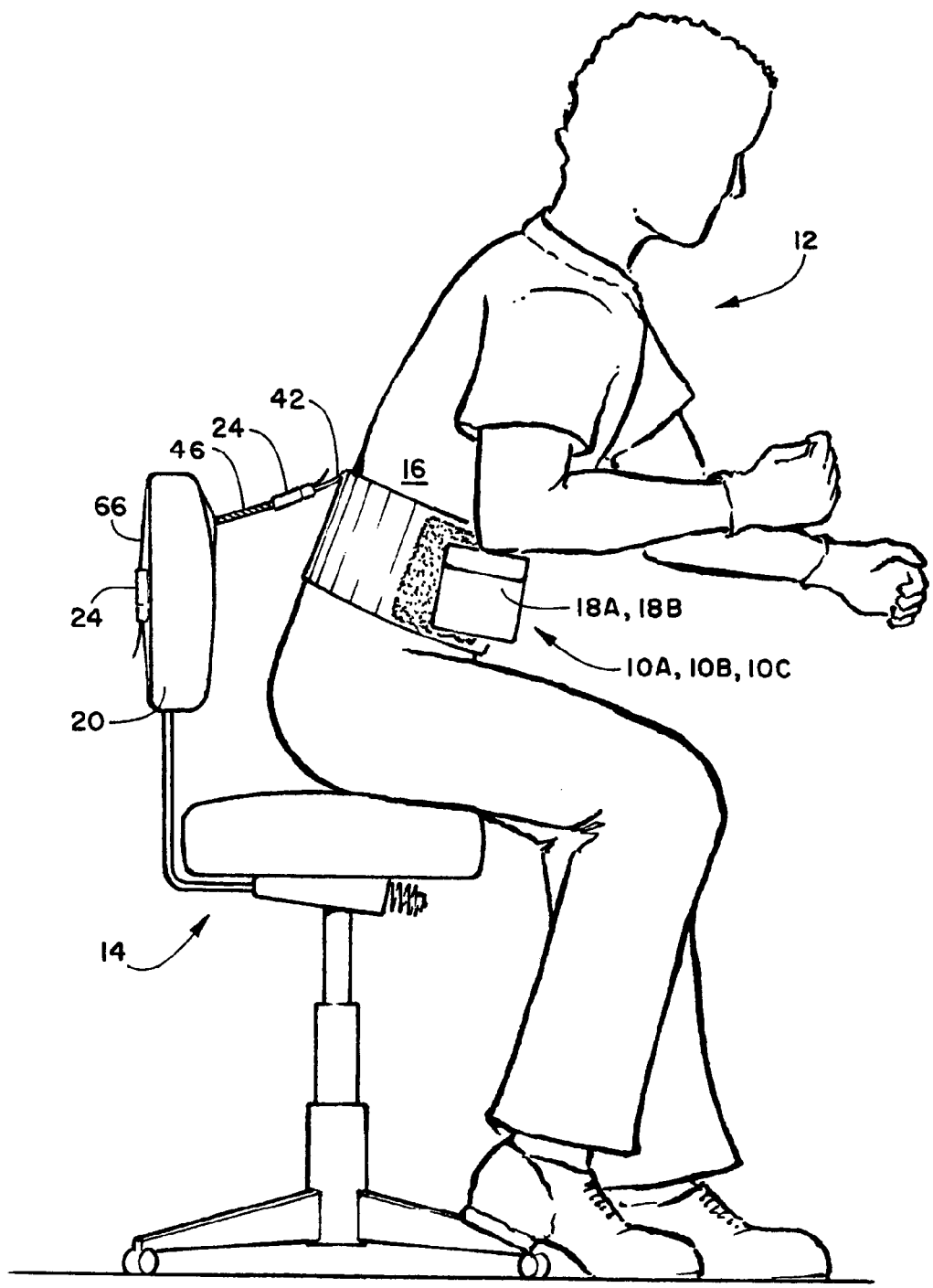
FIG. 8 depicts a side elevation of an individual sitting in a conventional office chair leaning forward with a flexible support between the chair and the preferred embodiment of the chair mounted lumbar and trapezius support system.

All of the embodiments of the device 10 shown and described herein can be attached to the chair 14 using a tether. This tether can be a means of attachment that is substantially stable using mounting straps 22 which hold the support belt 26 immediately adjacent to the chair 20, or should more forward movement be desired, a flexible support 46 can be added to the means of attachment of the support belt 26 to the chair 14. FIGS. 1 and 8 depict the attachment to the chair with the individual occupying the device 10. In cases where the user needs to constantly lean forward, it may be more desirous to provided a strap 42 of a fixed length to match the distance of forward lean, or it might be desirable to provide a flexible support 46 which would provide a means of rearward bias to the support belt 26. This would allow the user to lean forward with the added support of the flexible support 46, thus aiding the user in their forward lean to help prevent injury of strain or exhaustion of the back muscles that leaning can cause.

It therefore must be understood at this time that all the embodiments of the chair mounted lumbar and trapezius support system 10A, 10B, 1° C., and 10D, may be permanently or temporarily affixed to the chair 14 of any office style chair 14 either as an integral part of the chair 14, or using an attachment to the chair 14 such as straps 22, or using an elongated attachment such as strap 42, or using a flexible support 46 or combinations thereof as the comfort of the user and the conditions of the work to be done require. Further, the adjustable elbow rests 18A may be permanent or removable and optionally adjustable as to any of angle, horizontal position, vertical position, in any of the embodiments of the device as the use of the user may dictate.

Figure 7:
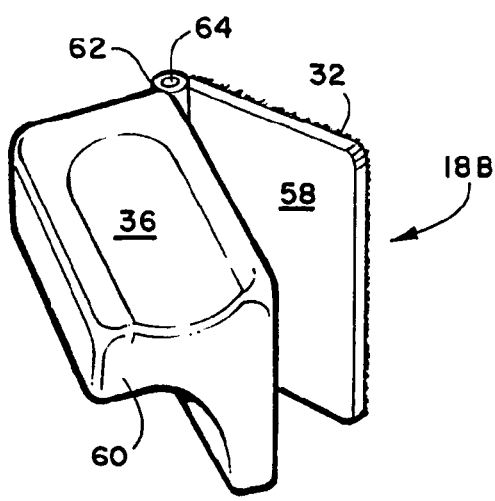
FIG. 7 depicts a perspective view of an alternate embodiment of the adjustable elbow rests that will pivot outwardly.

FIG. 7 depicts a perspective view of the right side of an alternate embodiment of the adjustable elbow-rest 18B that will pivot outwardly from the back. This alternate embodiment of the adjustable elbow rests 18B has a mounting plate 58 with the loop fastening surface 34 on the back and the rest member 60 pivoting outwardly from the back edge 62 of the mounting plate 56 by the means of the hinge mechanism 64. The left side of the adjustable elbow rest 18B will be a mirror image of the right side. The hinge mechanism 62 could be at the front of the adjustable elbow rest 18B allowing the adjustable elbow rests 18B to pivot from the front, or have a double hinge mechanism pivoting from both the front and back. Using this rotational engagement of the elbow rest 18B with its mount to any of the support belts 26 would provide a means of adjustment of the distance of the elbow rest 18B from the outside surface of the support belt 26 should the user need to place his elbow further from his side during use of the device 10.

FIG. 8 depicts a side elevation of an individual 12 sitting in a conventional office chair 14 leaning forward with a flexible support 46 between the chair backrest 20 and the embodiments of the chair mounted lumbar and trapezius support system 10A, 10B, 10C, or 10D. A separate set of chair backrest straps 66 or some other means of attachment of a fastener such as squeeze buckle 24 to the chair will be required to attach the flexible support 46 to the side squeeze buckle 24 on the strap 42. This or any of the other means of attachment of the support belt 26 to the chair 14 can be used as the comfort of the user and the job dictate.

Figure 9:
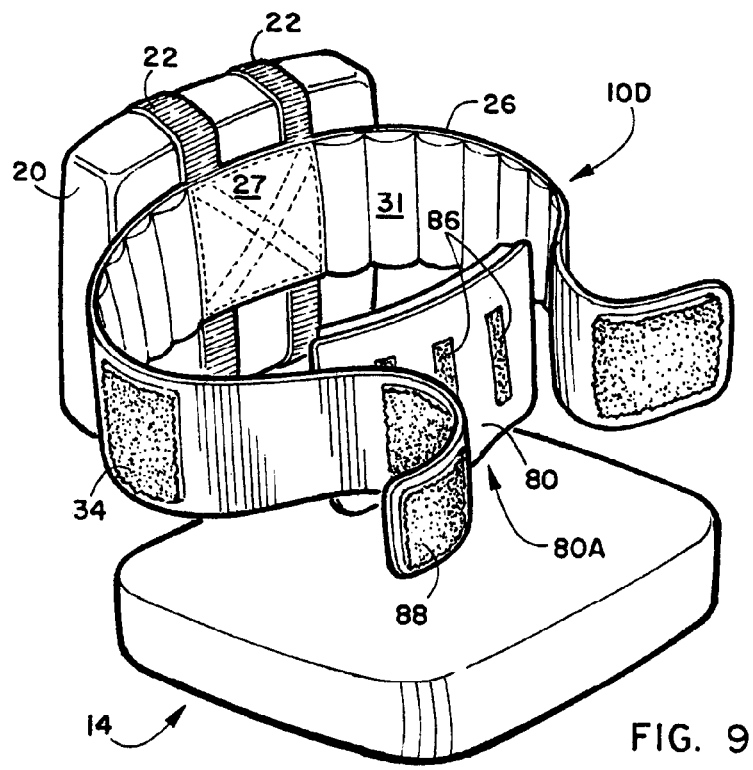
FIG. 9 depicts a perspective view of an additional preferred embodiment of the disclosed device featuring a support plate to provide abdominal support.
Figure 12:
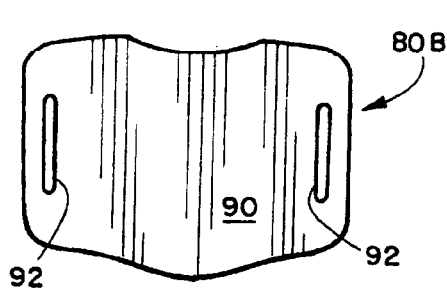
FIG. 12 is a rear view of the support plate showing a curved detent and slots as a means of attachment to the support belt.
Figure 10:
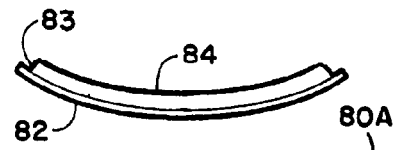
FIG. 10 is a top view of the support plate.
Figure 11:
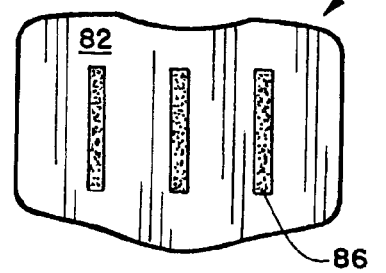
FIG. 11 is a front view of the support plate.

FIG. 9 depicts a perspective view of an additional preferred embodiment of the disclosed support system 10D featuring a support plate 80 to provide abdominal support to the wearer similar to that of torso support 54. However the support plate 80A would be substantially rigid and, as shown in a top view in FIG. 10 of the support plate 80A, it would have a front surface 82 and a pad 84 attached to the opposite rear surface. As shown in FIG. 11, on the front surface 82 would be a means for adjustable attachment of the distal ends of the support belt to the front surface 82 of the support plate 80 shown in the form of hook or loop fabric 86 configured to operatively engage the opposite hook or loop fabric 88 on the inside of the distal ends of the support belt 26. FIG. 12 is a rear view of the support plate showing a curved detent and slots as a means of attachment to the support belt. This removable engagement using the hook and loop fastener fabric of the support plate 80 with the support belt 26 also allows a means for vertical and horizontal adjustment of the attachment of the support plate 80 to the support belt 26.

Figure 13:
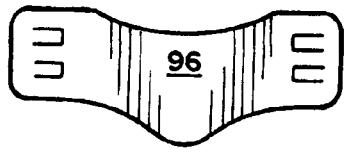
FIG. 13 is a smaller embodiment of the support plate.

FIG. 12 shows an alternate embodiment of the support plate 80B which has a protrusion 90 to allow for the anatomy of the user, and while it could mount to the support belt 26 much the same as support plate 80A, it is shown configured for a mount that would not engage in a mount with the support belt 26 but would instead attach around the torso of the user using a belt 52 through slots 92 in a mount to the user similar to that of the torso support 54 in FIG. 6. FIG. 13 is a smaller embodiment of the support plate 80B with a smaller protrusion 96.

Figure 14:
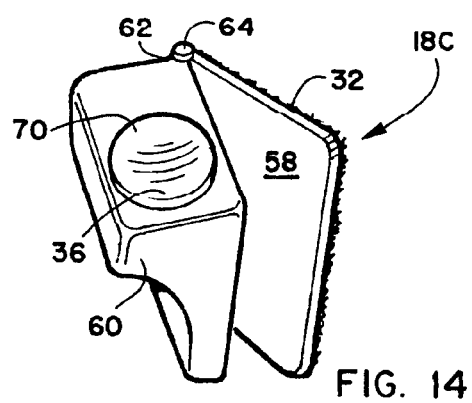
FIG. 14 depicts an additional preferred embodiment of the elbow support means which swivels to adjust for user positioning.

FIG. 14 depicts an additional preferred embodiment of the elbow support means similar to that of FIG. 7 in that it swivels on a hinge mechanism 64, thereby providing a means for adjustment of the distance of the elbow rest depression from the side of the support belt 26. This embodiment would provide a pad 70 made from a soft material such as rubber or foam and having a depression 36 formed therein to provide an elbow support.

The chair mounted back support system shown in the drawings and described in detail herein disclose arrangements of elements of particular construction and configuration for illustrating preferred and alternate embodiments of structure and method of operation of the present invention. While the present invention has been described herein with reference to particular embodiments thereof, a latitude of modifications, various changes and substitutions are intended in the foregoing disclosure, and it will be appreciated that in some instance some features of the invention will be employed without a corresponding use of other features without departing from the scope of the invention. It should also be understood, however, that elements of different construction and configuration and other arrangements thereof, other than those illustrated and described may be employed for providing a chair mounted support system in accordance with the spirit of this invention, and such changes, alternations and modifications as would occur to those skilled in the art are considered to be within the scope of this invention as broadly defined in the appended claims.

What is claimed is:

1. A chair mounted back support system comprising:
   a plurality of chairs;
   a support belt, said support belt having a center portion and having a first distal end and a second distal end;
   means of attachment of said first distal end to said second distal end;
   a tether attachable to a plurality of chairs and having an attachment to said support belt at a first tether end and having a second tether end;
   means of attachment of said second tether end to a rear of a said chair having a first fastener half attached to said second tether end and a second fastener half secured to said chair with said first half removably engageable with said second half with each of said plurality of chairs having a second half of said fastener secured thereto;
   said support belt securable around a torso of a user in an attached position, by attachment of said first distal end to said second distal end;
   said support belt providing a means to restrain a forward lean of said user when said user leans away from said rear of a said chair; and
   whereby said support belt in said attached position is removably attachable to any of said plurality of chairs allowing said user to move between any of said plurality of chairs and attach said tether thereto without removing said support belt from said attached position.

2. The chair mounted back support system of claim 1 additionally comprising:
   shoulder straps extending between said center portion of said support belt and said first distal end and said second distal end of said support belt.

3. A chair mounted back support system comprising:
   a support belt, said support belt having a center portion and having a first distal end and a second distal end, said support belt further having a first side surface defined by the area of said support belt between said first distal end and said center portion, and a second side surface defined by the area of said support belt between said second distal end and said center portion;
   means of attachment of said first distal end to said second distal end;
   at least one elbow support, said elbow support having a top surface, said top surface adapted for support of an elbow;
   means of attachment of said elbow support to said support belt to at least one of said first side surface or said second side surface of said support belt;
   means for angular adjustment of said top surface of said elbow support;
   a tether having an attachment to said support belt at a first tether end and having a second tether end;
   means of attachment of said second tether end to a rear of a chair;
   said support belt securable around a torso of a user in an attached position, by attachment of said first distal end to said second distal end; and
   said support belt providing a means to restrain a forward lean of said user when said user leans away from said rear of said chair.

4. The chair mounted back support system of claim 3 additionally comprising:
   shoulder straps extending between said center portion of said support belt and said first distal end and said second distal end of said support belt.

5. The chair mounted back support system of claim 3, additionally comprising:
   said support belt having a top edge and a bottom edge; and
   means for vertical adjustment of said top surface toward and away from said top edge.

6. The chair mounted back support system of claim 3, additionally comprising:
   means to rotate said elbow support toward and away from said support belt from an attachment point thereto.

7. The chair mounted back support system of claim 3, additionally comprising:
   said means of attachment of said second tether end to the rear of a chair comprising:
   a fastener, said fastener having a first half attached to said second tether end;
   said fastener having a second half, said second half secured to said chair; and
   said first half removably engageable with said second half.

8. The chair mounted back support system of claim 3, additionally comprising:
   means for horizontal adjustment of said top surface whereby said top surface may be translated toward or away from said center portion of said support belt.

9. The chair mounted back support system of claim 8, additionally comprising:
   said support belt having a top edge and a bottom edge; and
   means for vertical adjustment of said top surface toward and away from said top edge.

10. The chair mounted back support system of claim 9, additionally comprising:
    means to rotate said elbow support toward and away from said support belt from an attachment point thereto.

11. A chair mounted back support system comprising:
    a support belt, said support belt having a center portion and having a first distal end and a second distal end, said support belt further having a first side surface defined by the area of said support belt between said first distal end and said center portion, and a second side surface defined by the area of said support belt between said second distal end and said center portion;
    means of attachment of said first distal end to said second distal end;
    at least one elbow support, said elbow support having a top surface, said top surface adapted for support of an elbow;
    means of attachment of said elbow support to said support belt to at least one of said first side surface or said second side surface of said support belt;

means for horizontal adjustment of said top surface whereby said top surface may be translated toward or away from said center portion of said support belt;

a tether having an attachment to said support belt at a first tether end and having a second tether end;

means of attachment of said second tether end to a rear of a chair;

said support belt securable around a torso of a user in an attached position, by attachment of said first distal end to said second distal end; and said support belt providing a means to restrain a forward lean of said user when said user leans away from said rear of said chair.

12. The chair mounted back support system of claim 11, additionally comprising:

said means of attachment of said second tether end to the rear of a chair comprising:

a fastener, said fastener having a first half attached to said second tether end;

said fastener having a second half, said second half secured to said chair; and said first half removably engageable with said second half.

13. The chair mounted back support system of claim 11, additionally comprising:

means to rotate said elbow support toward and away from said support belt from an attachment point thereto.

14. The chair mounted back support system of claim 11, additionally comprising:

said support belt having a top edge and a bottom edge; and means for vertical adjustment of said top surface toward and away from said top edge.

* * * * *

UNITED STATES PATENT AND TRADEMARK OFFICE
CERTIFICATE OF CORRECTION

PATENT NO. : 6,893,098 B2
DATED : May 17, 2004
INVENTOR(S) : Kambiz Kohani

It is certified that error appears in the above-identified patent and that said Letters Patent is hereby corrected as shown below:

<u>Column 1,</u>
Line 65, delete "co" insert -- to --

<u>Column 9,</u>
Line 54, delete "1°" insert -- 10 --

Signed and Sealed this

Nineteenth Day of July, 2005

JON W. DUDAS
*Director of the United States Patent and Trademark Office*